US00PP19827P2

(12) United States Plant Patent
Bradford

(10) Patent No.: US PP19,827 P2
(45) Date of Patent: Mar. 17, 2009

(54) INTERSPECIFIC TREE NAMED 'BLACKRED II'

(50) Latin Name: ***Prunus* sp.**
Varietal Denomination: Blackred II

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,889

(22) Filed: Nov. 26, 2007

(51) Int. Cl.
*A01H 5/00* (2006.01)

(52) U.S. Cl. ..... Plt./180
(58) Field of Classification Search ..... Plt./180, Plt./184, 186
See application file for complete search history.

(56) References Cited

U.S. PATENT DOCUMENTS

PP13,478 P2 1/2003 Bradford
PP14,219 P2 10/2003 Bradford

*Primary Examiner*—Annette H Para
*Assistant Examiner*—June Hwu

(57) ABSTRACT

The present invention relates to an interspecific tree and more particularly to a new and distinct variety broadly characterized by a large size, vigorous, hardy, and productive tree. Being self-unfruitful, the present variety requires cross pollination from an apricot, interspecific, or plum that blooms during the early to mid season. The fruit matures under the ecological conditions described during mid June, with first picking on Jun. 9, 2007. The fruit is uniformly medium in size, dark purplish red in skin color, clingstone in type, oblate in shape, red in flesh color, firm in texture, and mildly acidic and sweet in flavor.

1 Drawing Sheet

Botanical classification: *Prunus* sp.
Varietal denomination: 'BLACKRED II'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Blackred II'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing an unpatented red plum, code named 19P442, was crossed by me in this manner. To pollinate this red plum, I selected bouquets from several sources of apricot and interspecific plum-apricot hybrid trees without keeping specific written details. Upon reaching maturity the fruit from this red plum tree was harvested and the seeds were removed, cracked, stratified and germinated as a group with the label "H5". They were grown as seedlings on their own root in my greenhouse and upon reaching dormancy transplanted to a cultivated area of my experimental orchard located near Le Grand, Calif. in Merced County (San Joaquin Valley). During the spring of 2004 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 19P442, by producing an abundant amount of fruit that is firm in texture and red in flesh color, but is distinguished therefrom by producing fruit that is sweeter in flavor and that matures about fifteen days earlier.

The present variety is similar to Yummybeaut (U.S. Plant Pat. No. 13,478) plum by being self-unfruitful and by producing fruit that is medium in size, that is firm in texture, that is clingstone in type, and that matures in mid June, but is distinguished therefrom by producing fruit that is darker in skin color, that is more oblate in shape, that has a less distinguishable suture, and that is red in flesh color instead of yellow.

SUMMARY OF VARIETY

The present interspecific variety is characterized by a large size, vigorous, hardy, and productive tree. Being self-unfruitful, the present variety requires cross pollination from an apricot, interspecific, or plum that blooms during the early to mid season. The fruit matures under the ecological conditions described during mid June, with first picking on Jun. 9, 2007. The fruit is uniformly medium in size, dark purplish red in skin color, clingstone in type, oblate in shape, red flesh color, firm in texture, and mildly acidic and sweet in flavor.

DRAWING

The accompanying photograph consists of four whole fruits positioned to display the characteristics of the skin color and form, one half of a fruit divided transversely to the suture plane to reveal the flesh and stone, a freshly cleaned stone, a young tip shoot growth, typical leaves, and three insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full ripe on Jun. 19, 2007, on the original tree during its sixth growing season. The flower and bud descriptions were developed during the previous blooming season. All major color code designations are by reference to the Inter-Society Color Council, National Bureau of Standards. Common color names are also used occasionally.

Parentage

Seed Parent: 19P442 plum (unpatented).
Pollen Parent: Unknown.

Tree

Size: Large, reaching and maintaining a height of 13' [3.96 m.] and a spread of 10' [3.05 m.] after six growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat Tolerance: Observed to perform adequately in typical central California climatic conditions, which typically include extended periods of heat.

Drought Tolerance: Variety is developed for commercial orchards and requires regular irrigation.

Production: Very productive, thinning usually necessary.

Fertility: Self-unfruitful, requiring cross pollination by a suitable early to mid seasonal blooming apricot, interspecific, or plum, such as 'Plumsweetone' (U.S. Plant Pat. No. 14,219).

Bearing: Regular bearer, with no crop failures observed.

Trunk:

- *Size.*—Medium, reaching a maximum diameter of 4½" [114 mm.] after the sixth growing season.
- *Texture.*—Shaggy.
- *Bark color.*—A Moderate brown [58. m.Br] and Strong brown [55. s.Br] variegation with Light yellowish brown [76. l.yBr] crevices present.
- *Lenticels.*—Approximate Number Per Square Inch: 10. Color: Light yellowish brown [76. l.yBr]. Average Size: ¼" [6.4 mm.]. Shape: Eye-shaped, elongated.

Branches:

- *Size.*—Diameter of limb is 3¼" [82.6 mm.] measured 12" above the crotch, 1¾" [44.5 mm.] measured 12" above the first fork.
- *Texture.*—Smooth on first and second year wood, increasing roughness with age.
- *Color.*—1st Year Wood Topside: Moderate olive brown [95. m.OlBr]. 1st Year Wood Underside: Brilliant yellow green [116. brill.YG]. Older Wood: A Light brown [57. l.Br] and Dark brown [59. d.Br] variegation.
- *Lenticels.*—Number Per Square Inch: More than 60 on second year wood. Color: Light yellowish brown [76. l.yBr]. Average Size: 1/32"[0.8 mm.]. Shape: Elongated, rectangular.

Leaves:

- *Size.*—Medium. Average Length: 3⅞" [98 mm.]. Average Width: 1⅝" [41 mm.].
- *Arrangement.*—Alternate.
- *Thickness.*—Medium.
- *Form.*—Elliptical.
- *Apex.*—Acuminate.
- *Base.*—Acute with an average angle base angle of 80 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ½" [12.7 mm.]. Average Thickness: 1/16" [1.6 mm.]. Color: Very yellow green [115. v.YG].
- *Stipules.*—Number: 2 per leaf, up to 6 per growing tip. Average Length: ¼" [6.4mm.]. Color: Brilliant yellow green [116. brill.YG]. becoming Moderate reddish brown [43. m.rBr] with age.
- *Glands.*—Number: Mostly 2 per leaf. Position: Alternately positioned at the intersection of the petiole and the leaf blade. Size: Small. Form: Globose. Color: Very yellow green [115. v.YG] becoming Deep reddish brown [41. deep rBr] in the center with age. Leaf buds: Pointed, medium.

Flower Buds:

- *Hardiness.*—Hardy, with respect to central California winters.
- *Diameter.*—Typically 3/16" [4.8 mm.] 1 week before bloom.
- *Length.*—Typically ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically thirty or more stamens, five sepals and petal locations alternately positioned.

- *Average flower diameter.*—15/16" [23.8 mm.].
- *Number of petals.*—Five, no double blossoms observed.
- *Petal shape.*—Oval to circular.
- *Petal margin.*—Entire, smooth to slightly wavy.
- *Average petal diameter.*—7/16" [11.1 mm.].
- *Average petal length.*—½" [12.7 mm.].
- *Petal apex.*—Rounded.
- *Petal base.*—Obtuse.
- *Petal color.*—White [263. White] on both sides.
- *Anther color.*—Strong orange yellow [68. s.OY].
- *Stigma color.*—Very greenish yellow [97. v.gY].
- *Sepal color.*—Strong yellow green [117. s.YG] with very slight Grayish pink [8. gy.Pk] tinge on the outer surface.
- *Sepal length.*—5/32" [4.0 mm.].
- *Sepal width.*—⅛" [3.2 mm.].
- *Sepal apex.*—Rounded to elliptical to match the width and length.

*Sepal margin.*—Fairly smooth.
*Average pistil length.*—⅝" [15.9 mm.].
*Average stamen length.*—½" [12.7 mm.].
*Fragrance.*—Moderate.
*Pollen production.*—Moderate.
*Blooming period.*—Early, two days before 'Ambra' plum (unpatented) plum.
*Onset of bloom.*—One percent on Feb. 20, 2007.
*Date of full bloom.*—Feb. 28, 2007.
*Duration of bloom.*—One to two weeks, dependent on ambient temperature.
*Bloom density.*—Medium to heavy.
*Number per cluster.*—2 to 10, average 5.

FRUIT

Maturity When Described: Full ripe, Jun. 9, 2007.
Date of First Picking: Jun. 9, 2007.
Date of Last Picking: Jun. 20, 2007.
Size: Uniform, Medium:
*Average diameter axially.*—2 1/16" [52.4 mm.].
*Average diameter across cheek plane.*—2 7/16" [61.9 mm.].
*Average diameter across suture plane.*—2 7/16"[61.9 mm.].
*Typical weight.*—4.4 ounces [125 grams].
*Form.*—Uniform, globose to oblate, symmetrical.
*Longitudinal section form.*—Round.
*Transverse section through diameter.*—Round to oblate.
Suture: A very shallow to almost indistinguishable trough extending from the base to the apex.
Ventral Surface: Rounded, no lipping.
Cavity: Flaring, rounded, suture showing on one side, Grayish reddish brown [46. gy.rBr] stem markings on some.
*Depth.*—3/16"[4.8 mm.].
*Breadth.*—⅞" [22.2 mm.].
Base: Truncate, slightly cordate if viewed parallel to the suture.
Apex: Rounded to truncate.
Pistil Point: An inconspicuous dot.
Stem: Medium.
*Average length.*—⅜" [9.5 mm.].
*Average width.*—5/64" [2.0 mm.].
Skin:
*Thickness.*—Medium.
*Surface.*—Smooth.
*Tenacity.*—Tenacious to the flesh.
*Astringency.*—Moderate.
*Tendency to crack.*—Slight.
*Color.*—Very dark purplish red [260. v.d.pR] with some very small Grayish pink [8. gy.Pk] freckling throughout.
*Bloom.*—Abundant.
Flesh:
*Color.*—Deep red [13. deep R] toward the stone, Very deep red [14. v.deep R] toward the skin.
*Surface of pit cavity.*—Covered with Very red [11. v.R] broken fibers when twisted away from the stone.
*Amygdalin.*—Moderate.
*Juice.*—Abundant, rich.
*Texture.*—Firm, crisp.
*Fibers.*—Abundant, fine, tender.
*Ripens.*—Slightly earlier toward the apex.
*Flavor.*—Mildly acidic and sweet, 15–19 brix.
*Aroma.*—Moderate.
*Eating quality.*—Good.

STONE

*Type.*—Clingstone.
*Form.*—Oval.
*Hilum.*—Narrow.
*Base.*—Straight.
*Apex.*—Obtuse with a 1/16" [1.6 mm.] tip.
*Sides.*—Equal.
*Surface.*—Rough throughout, a few ridges near the base, one groove on each side of the dorsal fin.
External Color of Stone: Moderate yellowish brown [77. m.yBr].
Pit Wall Color When Cracked: Pale orange yellow [73. p.OY].
Cavity Surface Color: Pale orange yellow [73. p.OY].
Average Pit Wall Thickness: 1/32" [0.8 mm.]
Average Width: ¾" [19.1 mm.].
Average Length: ⅞" [22.2 mm.].
Average Breadth: ¼" [6.4 mm.].
Tendency To Split: None observed.
Kernel:
*Form.*—Oval.
*Skin color.*—Dark orange yellow [72. d.OY] when dry.
*Pellicle color.*—Moderate yellowish brown [77. m.yBr].
*Vein color.*—Strong yellowish brown [74. s.yBr].
*Taste.*—Bitter.
*Viable.*—Yes.
*Average width.*—⅜" [9.5 mm.].
*Average length.*—½" [12.7 mm.].
*Amygdalin.*—Abundant.

Use

Market: Fresh market and long distance shipping.
Keeping Quality: Good, fruit quality observed to remain in good condition after 21 days in standard cold room at 36° Fahrenheit [2° Celsius].
Shipping quality: Good.
Resistance To Insects: No unusual susceptibilities noted.
Resistance To Diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to Yummybeaut (U.S. Plant Pat. No. 13,478) plum by being self-unfruitful and by producing fruit that is medium in size, that is firm in texture, that is clingstone in type, and that matures in mid June, but is distinguished therefrom by producing fruit that is darker in skin color, that is more oblate in shape, that has a less distinguishable suture, and that is red in flesh color instead of yellow.

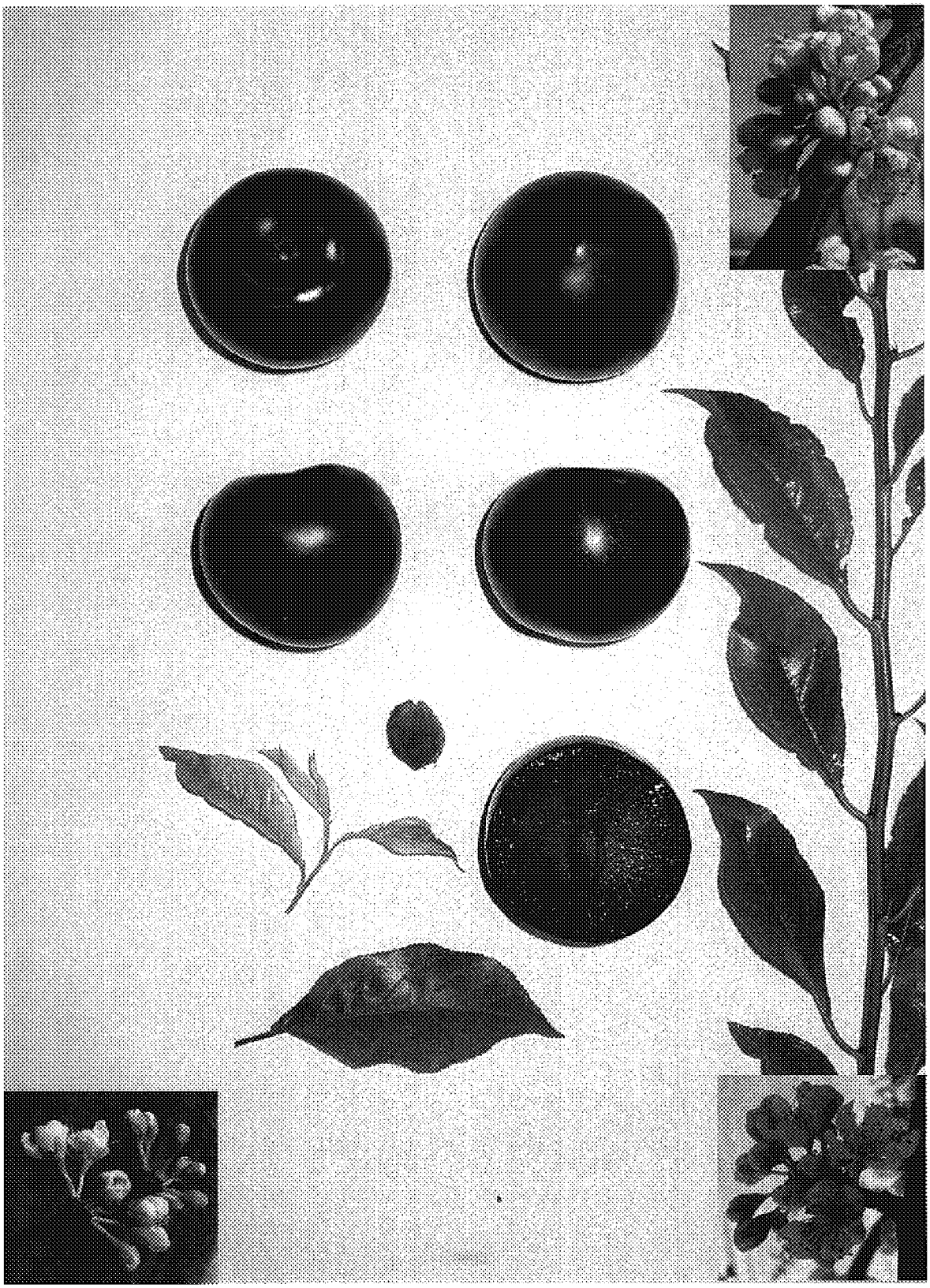

* * * * *